US010646980B2

(12) United States Patent
Allen et al.

(10) Patent No.: US 10,646,980 B2
(45) Date of Patent: May 12, 2020

(54) LUER LOCK TOOLS AND METHODS OF ASSEMBLING A LUER LOCK FITTING

(71) Applicant: Fresenius Medical Care Holdings, Inc., Waltham, MA (US)

(72) Inventors: Benjamin W. Allen, Novato, CA (US); Fidel L. Cajucom, Antioch, CA (US); Justin F. Pavoni, Jr., Pleasant Hill, CA (US); Hernando G. Garza, Concord, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 144 days.

(21) Appl. No.: 15/883,830

(22) Filed: Jan. 30, 2018

(65) Prior Publication Data

US 2018/0215016 A1    Aug. 2, 2018

Related U.S. Application Data

(60) Provisional application No. 62/452,573, filed on Jan. 31, 2017.

(51) Int. Cl.
*B25B 13/50*    (2006.01)
*B25B 27/10*    (2006.01)
(Continued)

(52) U.S. Cl.
CPC ............. *B25B 13/50* (2013.01); *A61M 5/347* (2013.01); *A61M 39/1011* (2013.01);
(Continued)

(58) Field of Classification Search
CPC ......... B25B 13/50; B25B 27/02; B25B 27/10; B23P 11/00; B23P 11/005; B23P 19/00;
(Continued)

(56) References Cited

U.S. PATENT DOCUMENTS

| 4,562,758 A | 1/1986 | Stirling |
| 4,845,827 A * | 7/1989 | Vandermast ............ B25B 27/02 29/280 |

(Continued)

FOREIGN PATENT DOCUMENTS

WO    2012106613    8/2012

OTHER PUBLICATIONS

International Search Report and Written Opinion dated (May 14, 2018), for PCT/US18/15936 (13 pages).

*Primary Examiner* — Bayan Salone

(57) ABSTRACT

Devices and methods for assembling a luer lock fitting (e.g., fitting for use in a hemodialysis and/or a peritoneal dialysis machine) may include a luer lock tool comprising a tool base including a grip portion adjacent a tool portion, the grip portion having an outer diameter and an internal cavity. The tool portion may have an internal cavity and may be configured to selectively receive and retain a male luer lock fitting at a first end of the cavity. A tool cap may have an outer diameter and an internal cavity. The tool cap may include a recessed portion at an end configured to selectively receive and retain a female luer lock fitting. The tool cap internal cavity may be configured to receive at least a portion of the tool portion of the tool base.

20 Claims, 9 Drawing Sheets

(51) Int. Cl.
  *B25B 27/02* (2006.01)
  *B25G 1/10* (2006.01)
  *A61M 39/10* (2006.01)
  *A61M 5/34* (2006.01)

(52) U.S. Cl.
  CPC .............. *B25B 27/02* (2013.01); *B25B 27/10* (2013.01); *B25G 1/102* (2013.01); *A61M 39/10* (2013.01); *A61M 2039/1027* (2013.01); *A61M 2205/583* (2013.01); *A61M 2205/586* (2013.01); *A61M 2207/00* (2013.01); *A61M 2207/10* (2013.01); *Y10T 29/53843* (2015.01); *Y10T 29/53874* (2015.01); *Y10T 29/53878* (2015.01); *Y10T 29/53909* (2015.01); *Y10T 29/53913* (2015.01); *Y10T 29/53943* (2015.01); *Y10T 29/53952* (2015.01); *Y10T 29/53987* (2015.01)

(58) Field of Classification Search
  CPC ........ B23P 19/04; B25G 1/102; A61M 5/347; A61M 39/1011; A61M 39/10; A61M 2039/1027; A61M 2205/583; A61M 2205/586; A61M 2207/00; A61M 2207/10; Y10T 29/53952; Y10T 29/53874; Y10T 29/53878; Y10T 29/53843; Y10T 29/53909; Y10T 29/53913; Y10T 29/53943
  USPC ......... 29/255, 278, 262, 263, 271, 270, 282; 604/410–414, 110, 523, 533, 27, 246, 604/159, 264; 206/366
  See application file for complete search history.

(56) References Cited

U.S. PATENT DOCUMENTS

| 7,024,968 | B2* | 4/2006 | Raudabough ......... A61M 5/347 81/121.1 |
| 8,684,994 | B2* | 4/2014 | Lev ...................... A61J 1/2089 604/405 |
| 2004/0193145 | A1 | 9/2004 | Raudabough et al. |
| 2010/0179489 | A1* | 7/2010 | Harding .............. A61M 39/045 604/256 |
| 2011/0048540 | A1 | 3/2011 | Stroup |
| 2012/0323210 | A1* | 12/2012 | Lev ...................... A61J 1/2089 604/405 |
| 2013/0035593 | A1* | 2/2013 | Lampropoulos .... A61M 13/003 600/432 |
| 2014/0135714 | A1* | 5/2014 | Verrilli ............... B29C 66/5344 604/264 |
| 2014/0276651 | A1* | 9/2014 | Schultz ............... A61M 39/165 604/535 |

\* cited by examiner

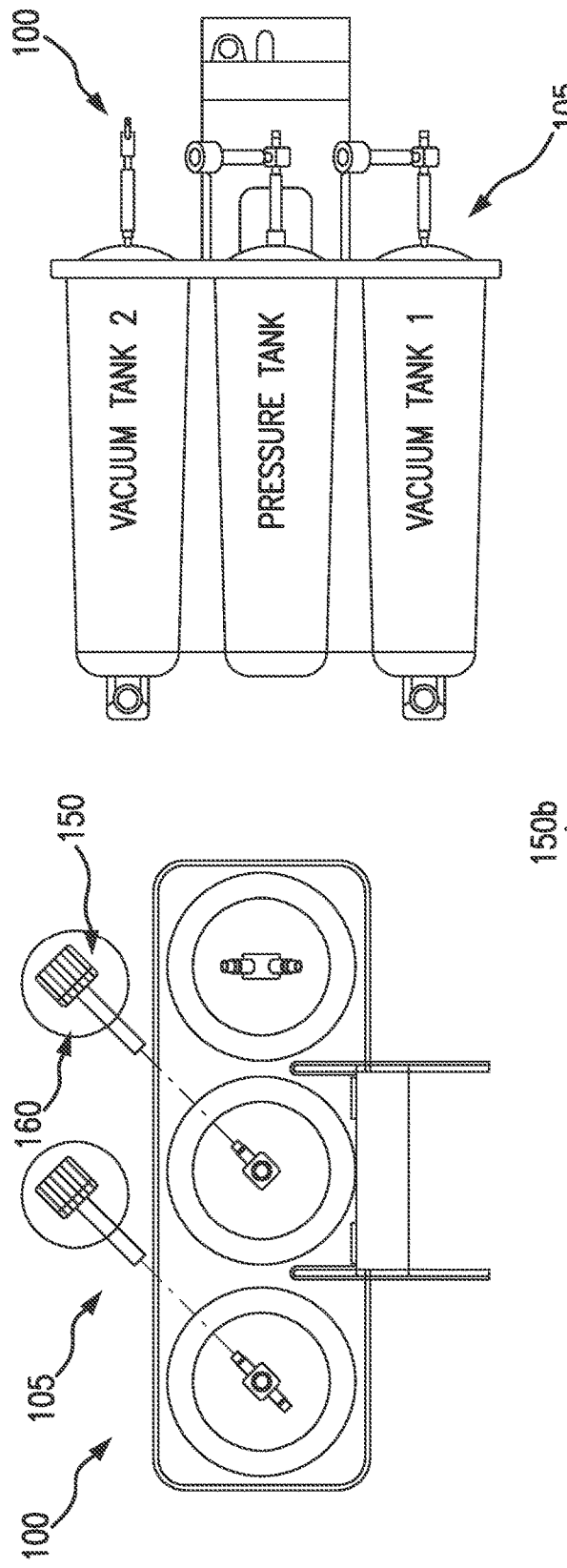
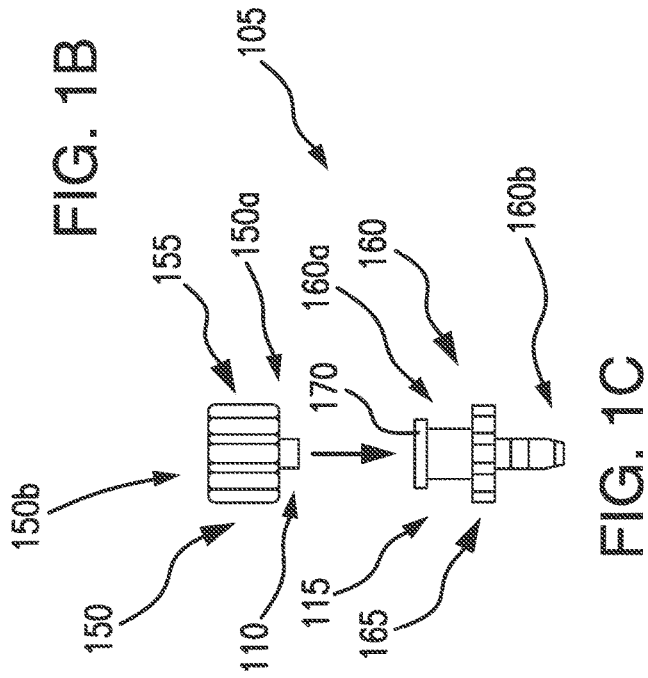
FIG. 1A
FIG. 1B
FIG. 1C

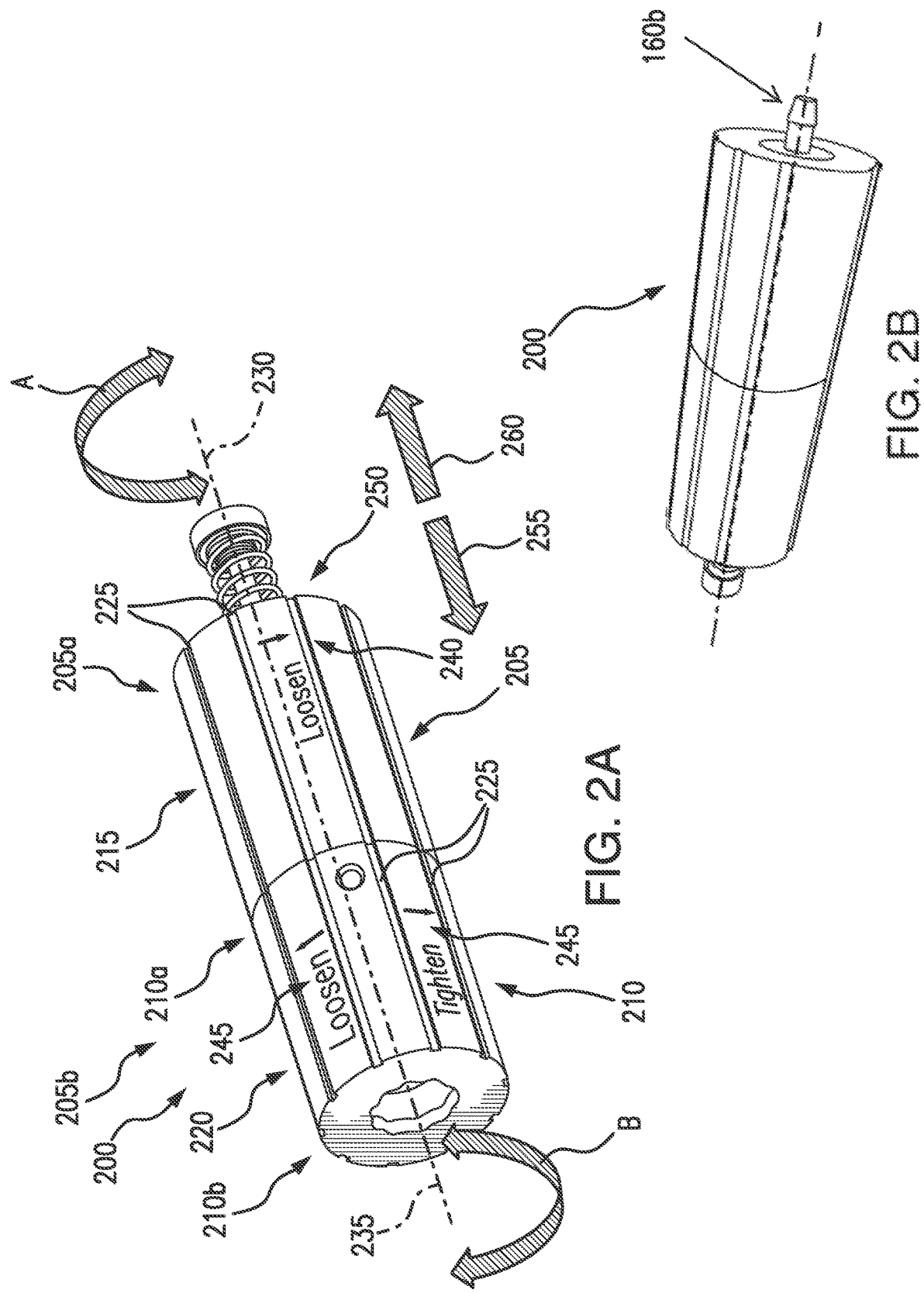

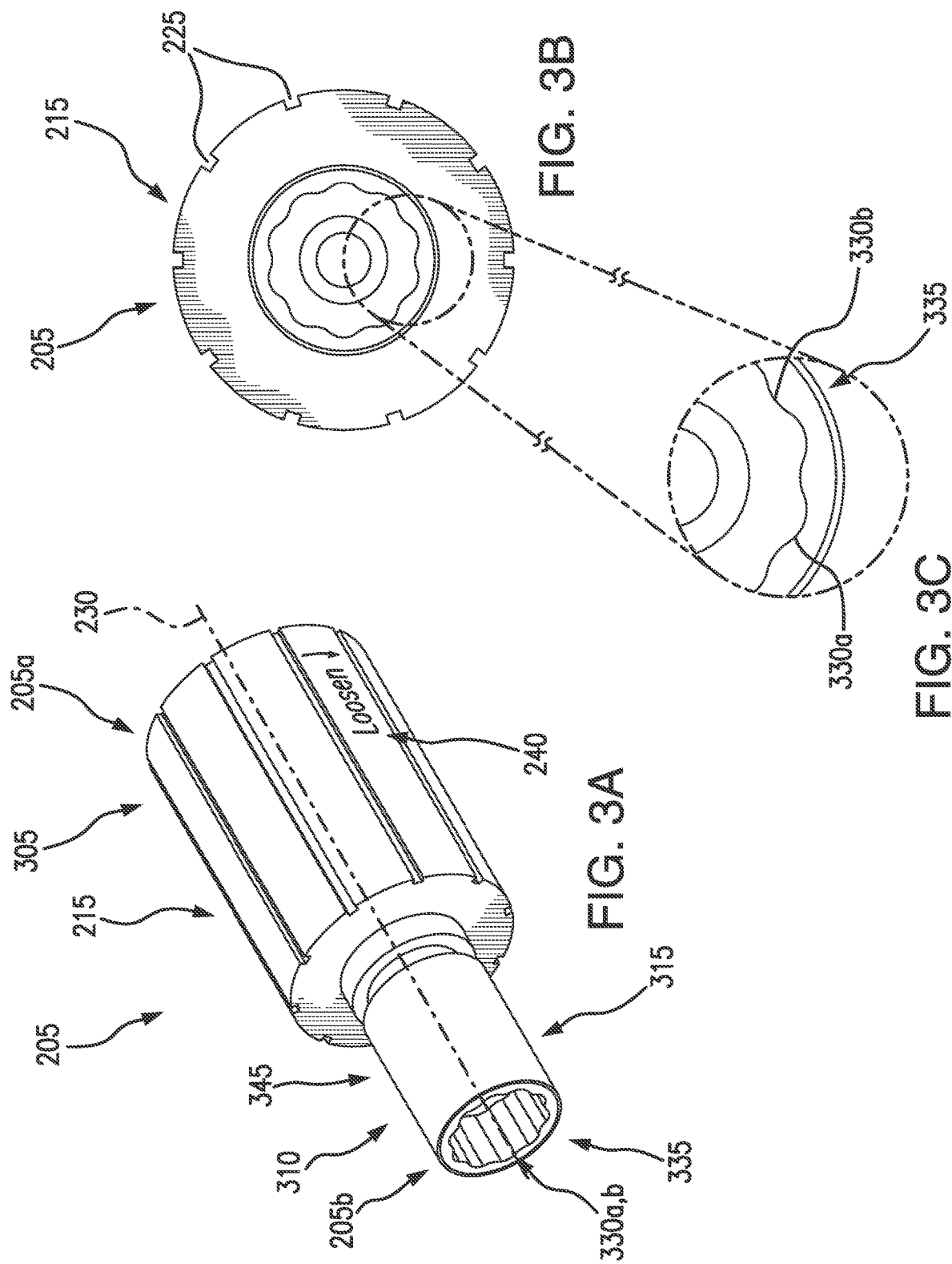

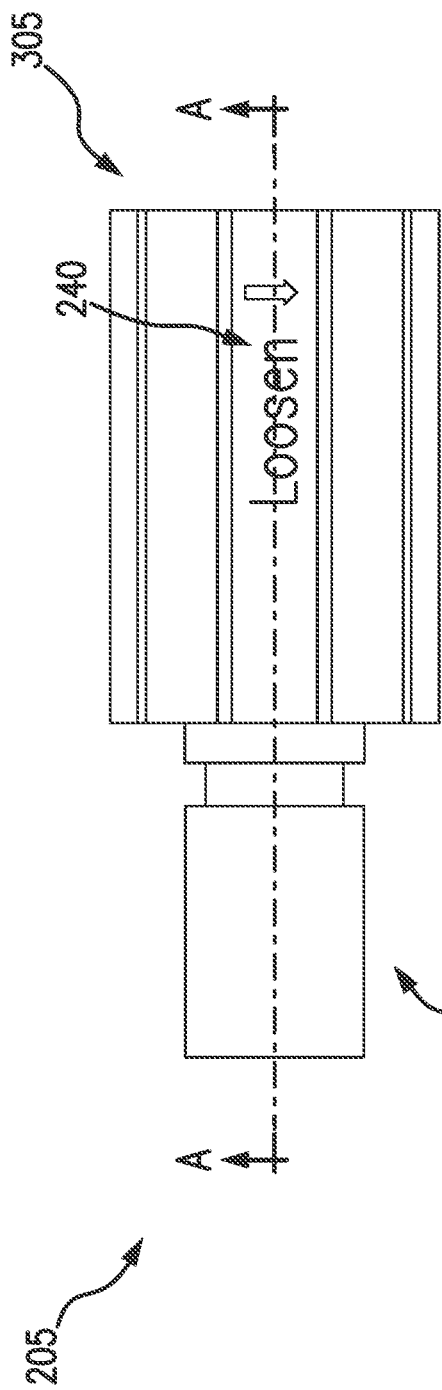
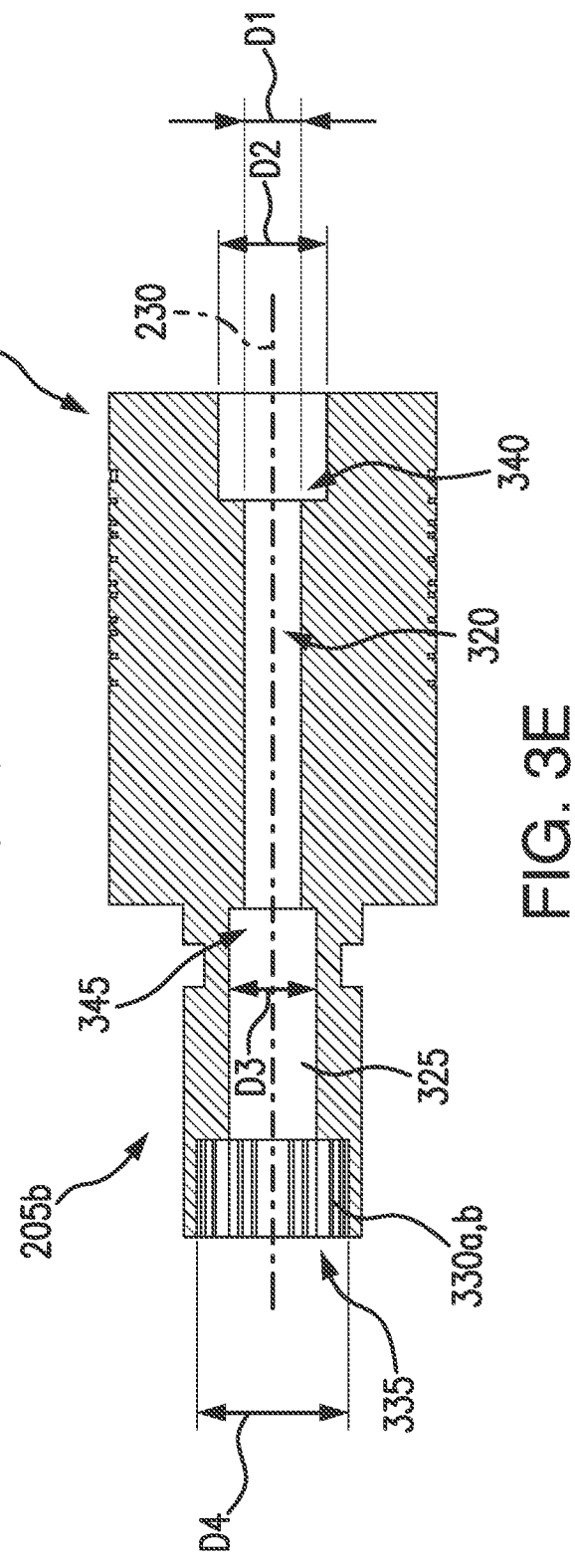
FIG. 3D
FIG. 3E

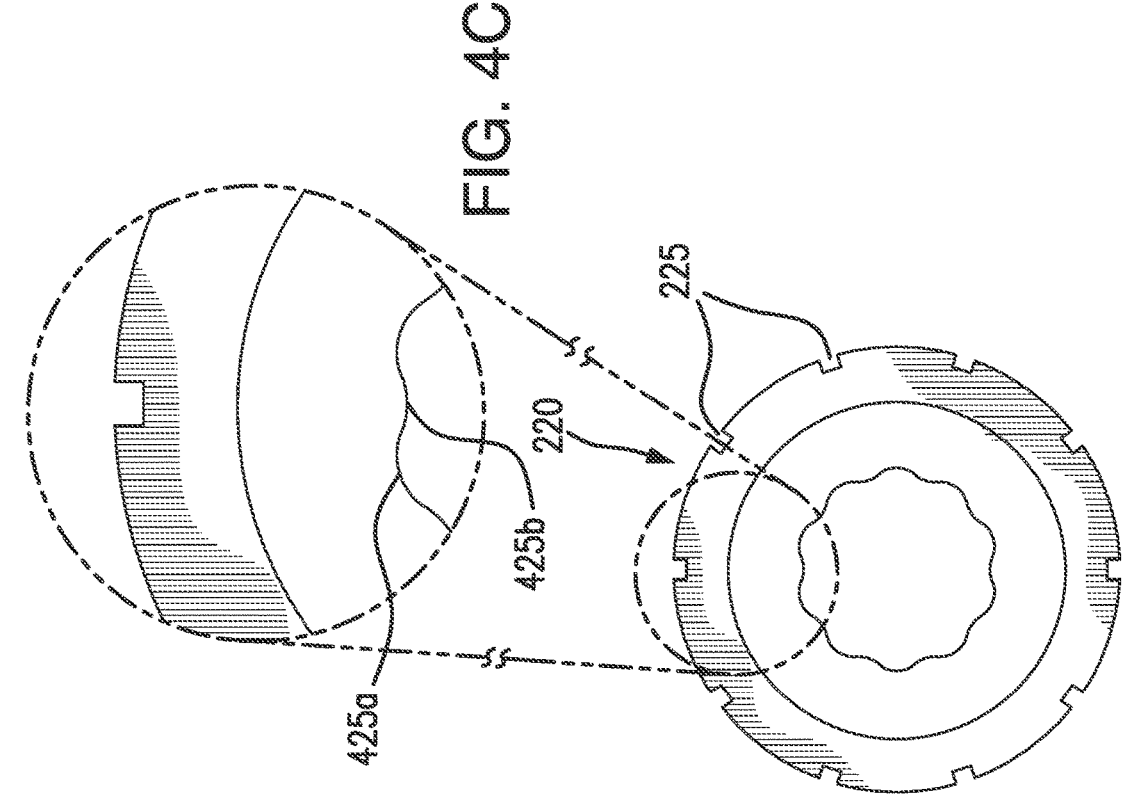
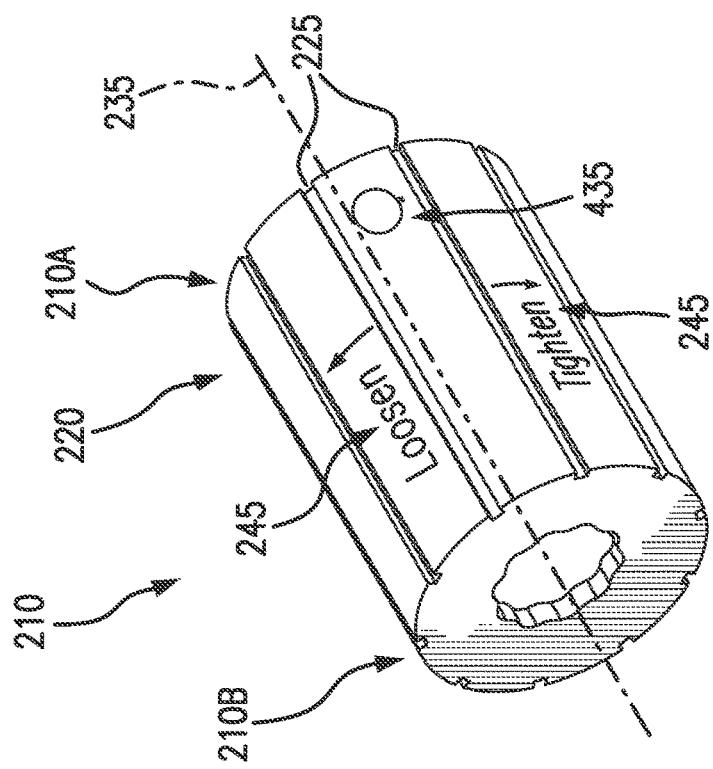

LUER LOCK TOOLS AND METHODS OF ASSEMBLING A LUER LOCK FITTING

CROSS-REFERENCE TO RELATED APPLICATIONS

This application is a nonprovisional patent application of, and claims priority to, U.S. Provisional Patent Application Ser. No. 62/452,573, filed Jan. 31, 2017, entitled "Luer Lock Tool," the entirety of which application is expressly incorporated by reference herein.

FIELD OF THE DISCLOSURE

The disclosure generally relates to a luer lock fitting assembly, and more particularly to a luer lock fitting assembly tool.

BACKGROUND

Dialysis machines are known for use in the treatment of renal disease. The two principal dialysis methods are hemodialysis (HD) and peritoneal dialysis (PD). During hemodialysis, the patient's blood is passed through a dialyzer of a hemodialysis machine while also passing dialysate through the dialyzer. A semi-permeable membrane in the dialyzer separates the blood from the dialysate within the dialyzer and allows diffusion and osmosis exchanges to take place between the dialysate and the blood stream. During peritoneal dialysis, the patient's peritoneal cavity is periodically infused with dialysate or dialysis solution. The membranous lining of the patient's peritoneum acts as a natural semi-permeable membrane that allows diffusion and osmosis exchanges to take place between the solution and the blood stream. Automated peritoneal dialysis machines, called PD cyclers, are designed to control the entire peritoneal dialysis process so that it can be performed at home, usually overnight, without clinical staff in attendance.

Luer lock-type fittings are known and may be used to achieve leak-free fluid connections in hemodialysis and/or peritoneal dialysis machines. Luer lock-type fittings 105 may be used in smaller scale fluid flow, for example, being sized to connect a fluid line to a pneumatic reservoir for pressure and vacuum chambers 100 in a hemodialysis and/or peritoneal dialysis machine, as shown in FIGS. 1A, 1B.

A luer lock-type fitting 105 may include a male luer lock fitting 150 and a female luer lock fitting 160 as illustrated in FIG. 1C, so that at least a portion 110 of a first end 150a of the male luer lock fitting 150 is receivable into at least a portion 115 of a first end 160a of the female luer lock fitting 160. The male luer lock fitting 150 may be connectable to tubing at a second end 150b, and a second end 160b of the female luer lock fitting 160 may be connectable to at least one of the pressure and vacuum chambers 100 in the hemodialysis and/or hemodialysis dialysis machine.

During manufacture of the hemodialysis and/or peritoneal dialysis machines and systems, the luer lock-type fittings 105 may be installed and removed several times throughout the manufacturing process. This may occur for one or more reasons, including but not limited to sub-assembly processes, testing and calibration procedures, and, if necessary, rework procedures. A plurality of luer lock-type fittings 105 may be incorporated on each hemodialysis and/or peritoneal dialysis machine, and with many devices being assembled each day, operators may be hand assembling and/or disassembling several hundred luer lock-type fittings 105 per day.

It may be disadvantageous to hand assemble and disassemble these fittings because operator error may be introduced by improperly, completely, and/or otherwise ineffectively tightening the connections, which may result in leaks in the pneumatic system. Additionally, over time this hand assembly and disassembly of several hundred luer lock fittings each day may cause musculoskeletal injury to operators, as it may be difficult to grip a small area of each of the male and female luer lock fittings to properly tighten and loosen as necessary. To avoid hand assembly and reduce hand/joint discomfort, makeshift tools (e.g., pliers, grips, etc.) may damage the components and still risk improper or incomplete tightening of the components such that leaks may still occur in the pneumatic reservoir.

It is with respect to these and other considerations that the present improvements may be useful.

SUMMARY

This Summary is provided to introduce a selection of concepts in a simplified form that are further described below in the Detailed Description. This Summary is not intended to necessarily identify key features or essential features of the claimed subject matter, nor is it intended as an aid in determining the scope of the claimed subject matter.

According to an exemplary embodiment of the present disclosure, a luer lock tool may include a tool base including a grip portion adjacent a tool portion, the grip portion having an outer diameter and an internal cavity, and the tool portion having an internal cavity that may be configured to selectively receive and retain a male luer lock fitting at a first end of the cavity, and a tool cap having an outer diameter and an internal cavity. The tool cap may include a recessed portion at an end configured to selectively receive and retain a female luer lock fitting. The tool cap internal cavity may be configured to receive at least a portion of the tool portion of the tool base.

In various of the foregoing and other embodiments of the present disclosure, the tool base and the tool cap may be configured to engage together such that a central axis of the tool base and a central base of the tool cap may be coaxial when the tool base and the tool cap are engaged. The recessed portion of the tool cap may be configured to contact a flange of the female luer lock fitting, the recessed portion having a plurality of protrusions and recesses configured to engage with corresponding recesses and protrusions of the flange. The tool portion of the tool base may be configured to contact the male luer lock fitting, the tool portion having a plurality of protrusions and recesses configured to engage with corresponding recesses and protrusions of the male luer lock fitting. One of the tool base and the tool cap may be configured to remain stationary and the other of the tool base and the tool cap may be configured to rotate about the respective central axis. The tool base and the tool cap may be configured to rotate in opposite directions about the respective central axis. Identification markings may be disposed on at least one of the grip portion outer diameter of the tool base and the tool cap outer diameter. A plurality of notches may be disposed on at least one of the grip portion outer diameter of the tool base and the tool cap outer diameter.

In various of the foregoing and other embodiments of the present disclosure, the luer lock tool may further include an ejection mechanism configured to selectively eject at least one of the male luer lock fitting and the female luer lock fitting. The ejection mechanism may include a rod and a spring, disposed coaxially at least partially in the tool portion cavity and the grip portion cavity of the tool base. The spring may be disposed adjacent a ledge in the grip portion cavity of the tool base and a cap may be coupled to an end of the rod, the cap and the end of the rod being disposed external to the tool base. The ejection mechanism may be configured to compress the spring such that the rod is configured to eject at least one of the male luer lock fitting and the female luer lock fitting out of the recessed portion end of the tool cap.

In various of the foregoing and other embodiments of the present disclosure, when the tool base and the tool cap are engaged, the tool portion of the tool base may be disposed adjacent the recessed portion of the tool cap. The tool base outer diameter and the tool cap outer diameter may be equal.

According to an exemplary embodiment of the present disclosure, a method for assembling a male luer lock fitting and a female luer lock fitting by a luer lock tool may include: inserting the male luer lock fitting in a tool portion of a tool base, the tool base including a grip portion adjacent a tool portion, and at least a portion of the tool portion configured to selectively receive and retain the male luer lock fitting; inserting the female luer lock fitting in a recessed portion of a tool cap, the recessed portion being configured to selectively receive and retain the female luer lock fitting; engaging the tool base and the tool cap by inserting the tool portion of the tool base in an internal cavity of the tool cap such that the tool portion of the tool base is adjacent the recessed portion of the tool cap and a central axis of the tool base is coaxial with a central axis of the tool cap, and the male luer lock fitting is receivable into the female luer lock fitting; and rotating one of the tool base and the tool cap about the respective central axis while holding the other of the tool base and the tool cap stationary, such that the male luer lock fitting and the female luer lock fitting are locked together by the rotation of the one of the tool base and the tool cap.

In various of the foregoing and other embodiments of the present disclosure, the method may further include ejecting the locked male luer lock fitting and the female luer lock fitting by an ejection mechanism. The ejection mechanism may include a rod and a spring. The rod and the spring may be disposed at least partially in an internal cavity of the tool base and an internal cavity of the tool cap and coaxial to the tool base and the tool cap, and a first end of the rod and the spring may be external to the tool base. The spring may extend externally along the rod, and the spring may be compressed between the first end of the rod and a ledge in an internal cavity of the tool base. A second end of the rod may be disposed at least partially in the internal cavity of the tool cap such that the rod pushes the locked male and female luer lock fitting out of the recessed portion of the tool cap. Protrusions of the male luer lock fitting may engage in recesses of the tool portion of the tool base, and recesses of the male luer lock fitting may engage in protrusions of the tool portion of the tool base. Protrusions of a flange of the female luer lock fitting may engage in recesses of the recessed portion of the tool cap, and recesses of the flange of the female luer lock fitting may engage in protrusions of the recesses portion of the tool cap.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures:

FIGS. 1A-1C illustrate a luer lock fitting and assembly in dialysis machines;

FIGS. 2A-2B illustrate perspective views of an exemplary embodiment of a luer lock tool configured in accordance with the present disclosure;

FIG. 3A illustrates a perspective view of an exemplary embodiment of a tool base of a luer lock tool configured in accordance with the present disclosure;

FIGS. 3B-3C illustrate front views of an exemplary embodiment of the tool base of FIG. 3A;

FIG. 3D illustrates a side view of an exemplary embodiment of the tool base of FIG. 3A;

FIG. 3E illustrates a section view of an exemplary embodiment of the tool base of FIG. 3D;

FIG. 4A illustrates a perspective view of an exemplary embodiment of a tool cap of a luer lock tool configured in accordance with the present disclosure;

FIGS. 4B-4C illustrate front views of an exemplary embodiment of the tool cap of FIG. 4A;

DETAILED DESCRIPTION

Figure 4D:
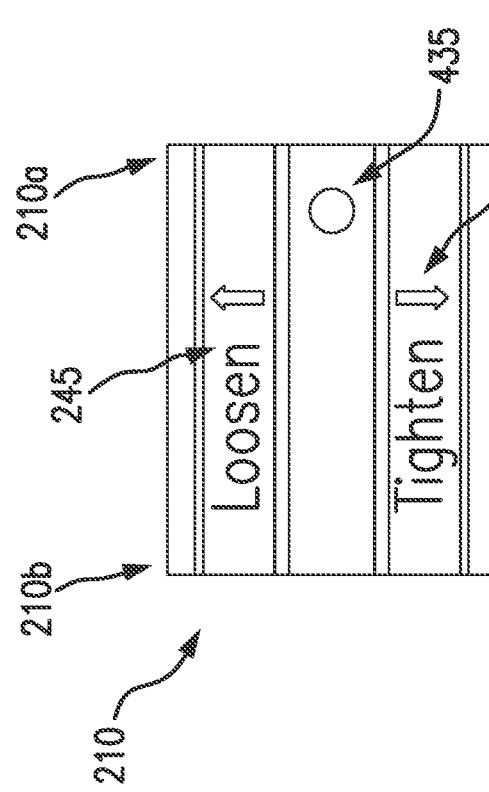
FIG. 4D illustrates a side view of an exemplary embodiment of the tool cap of FIG. 4A.
Figure 4E:
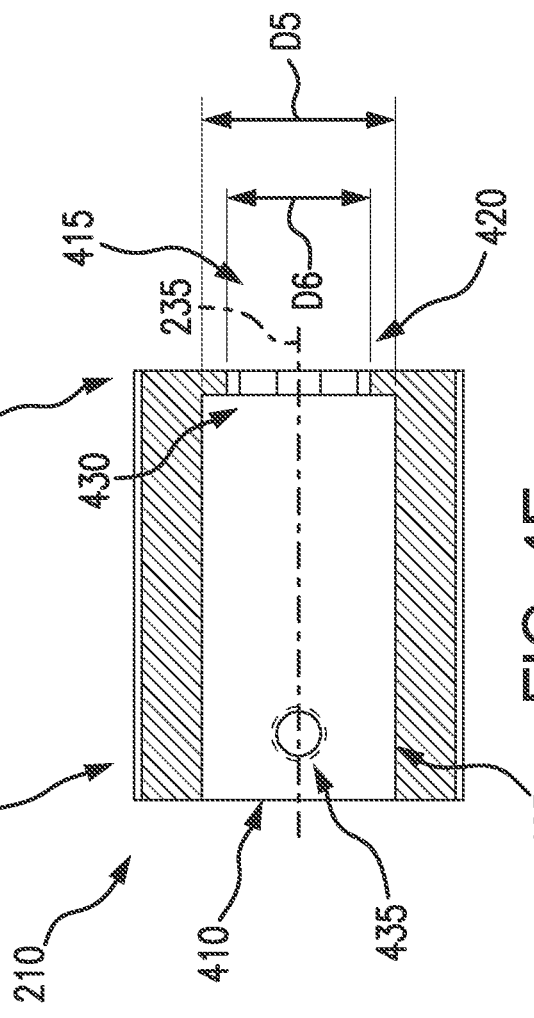
FIG. 4E illustrates a section view of an exemplary embodiment of the tool cap of FIG. 4D.

The present disclosure is not limited to the particular embodiments described herein. The terminology used herein is for the purpose of describing particular embodiments only, and is not intended to be limiting beyond the scope of the appended claims. Unless otherwise defined, all technical terms used herein have the same meaning as commonly understood by one of ordinary skill in the art to which the disclosure belongs.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps elements and/or components, but do not preclude the presence or addition of one or more other features, regions, integers, steps, operations, elements, components and/or groups thereof.

As described above, a plurality of luer lock fittings may be utilized in dialysis machines, e.g., hemodialysis and/or peritoneal dialysis machines, particularly, in a pneumatic reservoir subassembly for pressure and vacuum chambers of the dialysis machines. The luer lock fittings may be hand assembled and/or disassembled during the manufacturing process, so that operators may be handling several hundred luer lock fittings per day. The leur lock fittings may be small, for example, a grip 155 of the male luer lock fitting 150 and/or a grip 165 of the female luer lock fitting 160 may be less than 0.5 inches in diameter, and in some embodiments may be approximately 0.3 to 0.5 inches in diameter. This small diameter may result in operators employing a pinch grip to hold and/or rotate the luer lock fittings during assembly and/or disassembly. Over time, repeated use of a pinch grip may lead to discomfort in operator's hands and possible musculoskeletal injuries. Operators may also be driven to using unauthorized tools for assembly and/or disassembly of the luer lock fittings, which may result in leaks and potential machine defects. In the present disclosure, ergonomic assembly and/or disassembly tools for operators to utilize are described, which provide an accurate amount of tightening between the male and female luer lock fittings, such that leakage, e.g., leakage in the pneumatic reservoir of the pressure and vacuum chambers, may be prevented.

According to an embodiment of the present disclosure, a tool may be provided to assist in assembling and/or disassembling the male luer lock fitting 150 and the female luer lock fitting 160. Referring now to FIGS. 2A, 2B, an embodiment of a luer lock tool 200 is shown. The luer lock tool 200 may include a luer tool base 205 and a luer tool cap 210, configured to engage together with each other, and the male luer lock fitting and the female luer lock fitting, respectively. For example, the luer tool base 205 may include a first end 205a and a second end 205b, and the luer tool cap 210 may include a first end 210a and a second end 210b. In some embodiments, the second end 205b of the luer tool base 205 may be engageable with the first end 210a of the luer tool cap 210. When the tool base 205 and the tool cap 210 are engaged together, central axis 230 of the tool base 205 and central axis 235 of the tool cap 210 may be coaxial; that is, they share the same axis for alignment together. In some embodiments, the tool base 205 may be rotatable about the central axis 230 (as shown by arrow A) and the tool cap 210 may be rotatable about the central axis 235 (as shown by arrow B).

At least a portion of each of the tool base 205 and the tool cap 210 may be substantially cylindrical in shape. For example, the tool base 205 may extend along a central axis 230 and the tool cap may extend along a central axis 235. In some embodiments, the luer lock tool 200 may be approximately between 2 and 5 inches in length, and in some embodiments, the tool base 205 may be approximately 2 to 4 inches in length and the tool cap 210 may be approximately 1 to 3 inches in length. Although a cylindrical shape is illustrated for ease of grip for operators, it is understood that other shapes may be utilized as well, including but not limited to rectangular, pyramidal, and/or a shape having any number of sides so that an operator may hold the luer lock tool 200 by hand (see e.g., FIGS. 6A-6B). In some embodiments, the tool base 205 and/or the tool cap 210 may be formed of a metal, composite, and/or plastic material. For example, the tool base 205 and/or the tool cap 210 may be formed of aluminum and/or stainless steel. In some embodiments, the aluminum may be anodized.

At least a portion of the tool base 205 and the tool cap 210 may each have an outer diameter sized so that an operator may easily hold and/or handle each of the tool base and the tool cap. For example, at least a portion of the tool base 205 and the tool cap 210 may be about 1 inch in diameter. In some embodiments, an outer diameter of the tool base and the tool cap are the same, although different outer diameters are also envisioned. An outer diameter 215 of the tool base 205 and an outer diameter 220 of the tool cap 210 may include a plurality of notches 225, arranged circumferentially around the outer diameter 215, 220 of the tool base 205 and the tool cap 210 to increase an operator's grip on each of the tool base 205 and the tool cap 210. For example, the notches 225 may extend longitudinally in a straight line along the luer lock tool 200 as shown in FIGS. 2A-2B. However, it is understood that the notches 225 may extend longitudinally along the luer lock tool 200 (e.g., along the outer diameter 215 of the tool base 205 and/or along the outer diameter 220 of the tool cap 210) in a straight line, a non-linear pattern, a chevron pattern, a wave pattern, and/or any pattern that may improve an operator's grip on the luer lock tool 200.

Referring now to FIGS. 3A-3E, an embodiment of the luer tool base 205 in accordance with the present disclosure is shown. The tool base 205 may include a grip portion 305 extending along the central axis 230 (e.g., at the first end 205a) and a tool portion 310 (e.g., at the second end 205b) adjacent to and extending from the grip portion 405 along the central axis 230. The grip portion 305 may be sized so that the outer diameter 215 is equal to the outer diameter of the tool cap 210, and may include the plurality of notches 225 disposed circumferentially around the outer diameter 215. The tool portion 310 may have an outer diameter 345, and in some embodiments, the outer diameter 345 may be smaller than the outer diameter 215 of the tool base, and/or the outer diameter 220 of the tool cap 210. The outer diameter 345 may be a constant diameter, and may be receivable within the tool cap 210.

As shown in FIG. 3E, the grip portion 305 may include an internal cavity 320 extending along the central axis 230, and the tool portion 310 may include an internal cavity 325 extending along the central axis 230. The internal cavities 320, 325, may be adjacent to each other to form a through hole in the tool base 205. In some embodiments, the internal cavity 320 may have a constant inner diameter, and in other embodiments, the internal cavity 320 may include a step between a first inner diameter D1 and a second inner diameter D2, and include a ledge 340 therebetween. In some embodiments, the internal cavity 325 may have a constant inner diameter, and in other embodiments, the internal cavity 325 may include a step between a third inner diameter D3 and a fourth inner diameter D4, in which the fourth diameter D4 may be a recess 335 at the second end 205b of the tool base 205. The diameters D1-D4, as will be described below and with respect to FIG. 5, may be sized for receiving one or more internal components, e.g., an ejection mechanism 250 which may extend at least partially beyond the first end 205a of the tool base 205.

The tool portion 310 may be configured to engage with a male luer lock fitting 150. For example, according to an illustrated embodiment shown in FIG. 1C, the male luer lock fitting 150 (e.g., at the second end 150b of the male luer lock fitting 150) may include a patterned grip 155. The grip 155 may be shaped in any known manner, including but not limited to a nut, a knurled grip, or a plurality of protrusions and recesses, or combinations thereof. At least a portion of the internal cavity 325, e.g., recess 335, of the tool portion 310 may be configured to match the pattern of the grip 155, so that the tool portion 310 is engageable with the grip 155 by the fourth inner diameter D4. For example, the male luer lock fitting 150 may fit within the recess 335 at an end 315 of the tool portion 310 (e.g., at the second end 205b of the tool base 205). In some embodiments, protrusions 330a on the tool portion 310 may engage in recesses of the grip 155, and recesses 330b of the tool portion 310 may engage with protrusions of the grip 155. That is, the fourth inner diameter D4 may be variable, e.g., between protrusions and recesses 330a, 330b, as shown in FIGS. 3B-3C. In some embodiments, the inner diameter D4 may vary between the protrusions and recesses 330a, 330b by approximately 0.02 to 0.05 inches.

The tool base 205 may be configured so that a male luer lock fitting 150 may be insertable in the recess 335 of the tool portion 310 of the tool base 205, such that the tool portion 310 selectively receives and retains the male luer lock fitting 150. As described in detail below, the tool portion 310 may be configured to be at least partially receivable within the tool cap 210.

Referring now to FIGS. 4A-4E, an illustrated embodiment of a luer tool cap 210 according to the present disclosure is shown. As described above, the tool cap 210 may have an outer diameter 220, and an inner diameter 405, forming a cavity 410 extending along the central axis 235 and configured to receive at least a portion of the tool portion 310 of the tool base 205. The tool cap 210 may be sized so that the outer diameter 220 is approximately equal to the outer diameter 215 of the tool base 205, and may include the plurality of notches 225 disposed circumferentially around the outer diameter 220.

In embodiments, the second end 210b of the tool cap 210 may include a recessed portion 420 of the cavity 410. In some embodiments, the cavity 410 may be a constant inner diameter 405, or include a step 430 between a fifth inner diameter D5 and a sixth inner diameter D6, and may have an open end 415, e.g., at the second end 210b of the tool cap 210. The fifth inner diameter D5 may be a constant diameter. The sixth inner diameter D6 may form the recessed portion 420, and may have a variable diameter. In some embodiments, the fifth inner diameter D5 may be sized to receive the tool portion 310 of the tool base 205.

The recessed portion 420, e.g., the sixth inner diameter D6, may be configured to receive at least a portion of a female luer lock fitting 160. For example, the female luer lock fitting 160 may include a flange 165. The flange 165 may have a patterned grip, e.g., a plurality of protrusions and recesses, or a knurled pattern, or have a shape of a standard nut, or combinations thereof. The recessed portion 420 of the tool cap 210 may be configured to match the pattern of the flange 165 of the female luer lock fitting 160, so that the tool cap 210 is engageable with the flange 165 by the sixth inner diameter D6. For example, the female luer lock fitting 160 may fit within the recessed portion 420 at the second end 210b of the tool cap 210. In some embodiments, protrusions 425b may engage in recesses of the flange 165, and recesses 425a of the tool cap 210 may engage with protrusions of the flange 165, so that the lock cap 210 selectively receives and retains the female luer lock fitting 160. That is, the sixth inner diameter D6 may be variable, e.g., between protrusions and recesses 425a, 425b, as shown in FIGS. 4B-4C. In some embodiments, the sixth inner diameter D6 may vary between the protrusions and recesses 425a, 425b by approximately 0.02 to 0.05 inches.

The recessed portion 420 may be engageable with the flange 165. For example, the recessed portion 420 may be configured such that protrusions on the flange 165 engage with recesses 425a in the recessed portion 420, and recesses on the flange 165 engage with protrusions 425b in the recessed portion 420, so that the lock cap 210 selectively receives and retains the female luer lock fitting 160. When the flange 165 engages with the recessed portion 420 of the tool cap 210, at least a portion of the female luer lock fitting 160, e.g., the second end 160b of the female luer lock fitting 160, may extend beyond the tool cap 210 (see e.g., FIGS. 2B, 6A).

In an assembly process, an operator may insert the male luer lock fitting 150 in the luer tool base 205, and the female luer lock fitting 160 in the luer tool cap 210 as described above. The tool base 205 and the tool cap 210 may then be assembled together, with the tool portion 310 of the tool base 205 being at least partially inserted in the cavity 410 of the tool cap 210. In some embodiments, an aperture 435 may extend radially from the outer diameter 220 of the tool cap 210 to the cavity 410, and may be configured to receive a stop (see FIG. 5), e.g., a bolt, a screw, a pin, or the like that may fixedly attach, e.g., lock, the tool base 205 and the tool cap 210 together.

When the tool base 205 and the tool cap 210 are coupled, the male luer lock fitting 150 and the female luer lock fitting 160 are coaxial and may be disposed adjacent to each other so that they may be attached to each other. For example, at least a portion of the male luer lock fitting may be receivable into the female luer lock fitting. A lip 170 of the female luer lock fitting 160 may engage in a thread (not shown) of the male luer lock fitting 150 when the tool base 205 and the tool cap 210 are coupled together.

To lock and/or unlock, e.g., assemble and/or disassemble, the male luer lock fitting 150 and the female luer lock fitting 160, the operator may hold the tool cap 210 stationary while rotating the tool base 205 about the central axes 230, 235 as shown by arrow A, such that the lip 170 of the female luer lock fitting 160 is threaded and/or unthreaded to the male luer lock fitting 150. In some embodiments, the tool base 205 may be held stationary while the tool cap 210 is rotated about the central axes 230, 235 as shown by arrow B. When disassembling the male and female luer lock fittings 150, 160, one of the tool base 205 and the tool cap 210 may be held stationary while the other of the tool base 205 and the tool cap 210 may be rotated. In other embodiments, the tool base 205 may be rotatable in one direction, and the tool cap 210 may be rotatable in an opposite direction about the central axes 230, 235 to assemble and/or disassemble the male and female luer lock fitting 150, 160. As shown in the callout of FIG. 1A, when the luer lock fitting 105 is assembled, at least a portion of the male luer lock fitting 150 is adjacent to at least a portion of the female luer lock fitting 160, and at least a portion of the male luer lock fitting 150 is received within the female luer lock fitting 160. For example, the grip 155 of the male luer lock fitting 150 may be adjacent to the flange 165 of the female luer lock fitting 160, and the portion 110 of the male luer lock fitting 150 may be received within the portion 115 of the female luer lock fitting 160.

As shown in the illustrated embodiments, the tool base 205 and/or the tool cap 210 may include identification, or visual, markings to assist operators in assembling and/or disassembling the male and female luer lock fittings. This may ensure the male and female luer lock fittings are uniformly tightened so that leaks may be prevented when assembled in the dialysis devices. For example, visual markings 240 on the outer diameter 215 of the tool base 205 may include one or more letters, words, symbols, or combinations thereof, to indicate which direction the tool base 205 should be rotated to achieve desired assembly and/or disassembly of the male and female luer lock fittings 150, 160. Similarly, visual markings 245 on the outer diameter 220 of the tool cap 210 may include one or more letters, words, symbols, or combinations thereof, to indicate which direction the tool base 205 is rotatable to achieve desired assembly and/or disassembly of the male and female luer lock fittings 150, 160. In some embodiments, the visual markings 240, 245 may be etched or engraved into the respective outer diameter 215, 220 of the tool base 205 and/or the tool cap 210. In some embodiments, markings may be utilized to indicate degree of rotation in addition to direction, and may be calibrated to correspond to given degrees of the tightness of the male and female luer lock fittings.

Providing a luer lock tool in accordance with the present disclosure as described may be advantageous in providing an operator a safe and quick process to assemble and/or disassemble the male and female luer lock fittings 150, 160. The luer lock tool 200 may be an ergonomic solution for operators by providing a larger gripping area for the operator to hold while rotating one of the tool base 205 and/or the tool cap 210. In this manner, operators are no longer holding a small area of the male and female luer lock fittings (e.g., the grip 155 and/or the flange 165), thereby helping to reduce long-term stress and injury in fingers and hands joints. Additionally, the luer lock tool 200 may provide a uniform locking of the male and female luer lock fittings when assembled. In some embodiments, the notches 225 on the tool base 205 and the tool cap 210 may be used as alignment features so that an operator may rotate one of the tool base 205 and the tool cap 210 to a standard uniform rotation. A stop 530 (see FIG. 5) may be incorporated in either or both of the tool base 205 and tool cap 210, e.g., through the aperture 435 of the tool cap 210 to engage against tool portion 310 of the tool base 205, to ensure consistent rotation without over-rotation. The notches 225 and/or stops 530 may be advantageous to ensure proper assembly of the tool base 205 and the tool cap 210 so that assembly of the luer lock fitting 105 may prevent pneumatic leaks.

Figure 5:
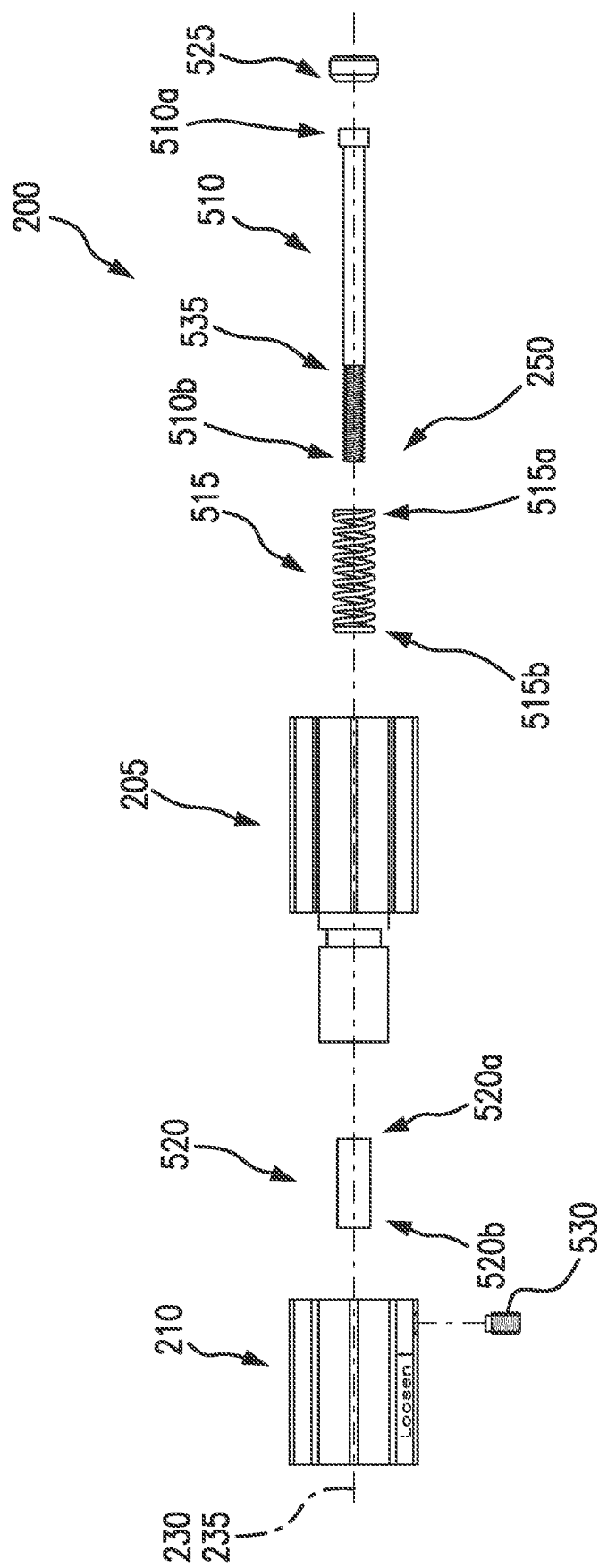
FIG. 5 illustrates an exemplary embodiment of an explosion view of a luer tool lock configured in accordance with the present disclosure.

In some embodiments, an ejection mechanism for ejecting at least one of the male and female luer lock fittings 150, 160 from the luer lock tool 200 may be included. Referring now to FIG. 5, an explosion view of an embodiment of a luer lock tool 200 according to the present disclosure is shown. As shown, an ejection mechanism 250 may be disposed in the tool base 205. The ejection mechanism 250 may be coaxial with the tool base 205 and the tool cap 210, e.g., extending along the central axes 230, 235. In some embodiments, the ejection mechanism 250 may include a rod 510, a spring 515, a sleeve 520, and a cap 525, although the ejection mechanism may be any known spring and rod or other configuration.

In embodiments, the rod 510 may extend along central axis 230, 235 and may be disposed substantially along the length of the internal cavities 320, 325 of the tool base 205, with a first end protruding externally from the tool base 205. The cap 525 may be coupled to the rod at a first end 510a of the rod 510, as shown in FIGS. 2A, 2B, for example, by press fit. In some embodiments, the cap 525 may be coupled to the rod 510 by adhesive, solder, welding, brazing, and/or a mechanical fastener, including but not limited to screws, threads, pin, groove, rivet, and the like. A second end 510b of the rod 510 may be disposed internally in the tool portion 310 of the tool base 205 and may be coupled to sleeve 520. In some embodiments, the second end 510b of the rod 510 and the sleeve 520 may be screwed together by threads 535. The sleeve 520 may be disposed in the third inner diameter D3 of the cavity 325. In some embodiments, the cavity 325 and the cavity 320 may have different diameters. For example, at least a portion of the cavity 325 may have a third inner diameter D3, and at least a portion of the cavity 320 may have a first inner diameter D1, where the first inner diameter D1 is less than the third inner diameter D3, and a ledge 345 is formed between the cavities 320 and 325. In some embodiments, a first end 520a of the sleeve 520 may abut the ledge 345, so that the rod 510 is restrained from being fully removable from the tool base 205 in the longitudinal direction along the central axes 230, 235. For example, the sleeve 520 coupled to the second end 510b of the rod 510 may be movable in the longitudinal direction along the central axis 230, 235 within the cavity 325 in the direction indicated by arrow 255 (see FIG. 2A), but may be at least partially constrained by the ledge 345 from moving in the opposite direction, as indicated by arrow 260.

A spring 515 may also be disposed at least partially in the cavity 320 of the tool base 205. In some embodiments, the spring 515 may be a helical spring, and extend along central axis 230, 235 such that the rod 510 may extend internally through the spring 515. A first end 515a of the spring 515 may be adjacent the cap 525, and a second end 515b of the spring 515 may abut a ledge 340 in the internal cavity 320 of the grip portion 305 of the tool base 205. In some embodiments, the cap 525, the first end 515a of the spring 515, and the first end 510a of the rod 510 may extend out of the cavity 320 beyond the first end 205a of the tool base 205. As described above, the cavity 340 may be formed in the cavity 320 between a first inner diameter D1 and a second inner diameter D2, in which the first inner diameter D1 may be smaller than the second inner diameter D2. For example, the first inner diameter D1 may be sized to receive the rod 510 (e.g., a slip fit or loose fit), the second inner diameter D2 may be sized to receive the first end 510a of the rod 510 and the spring 515 (e.g., a slip fit or loose fit), and the third inner diameter D3 may be sized to receive the second end 510b of the rod 510 and the sleeve 520 (e.g., a slip fit or loose fit).

The rod 510 may be movable within the cavity 320 in the longitudinal direction along the central axis 230, 235, by the compression and tension of the spring 515. For example, when the rod 510 and the sleeve 520 are moved in the direction indicated by arrow 255, the second end 515b of the spring 515 may abut and compress against the ledge 340. When the rod 510 is released, the compression force of the spring 515 may move the rod 510 and the sleeve 520 in the direction indicated by arrow 260 until the first end 520a of the sleeve 510 abuts the ledge 345. The ejection mechanism 505 may be movable, for example, by an operator pressing on the cap 525 to eject an individual male luer lock fitting 150, an individual female luer lock fitting 160, and/or an assembled luer lock fitting 105.

Figures 6A, 6B:
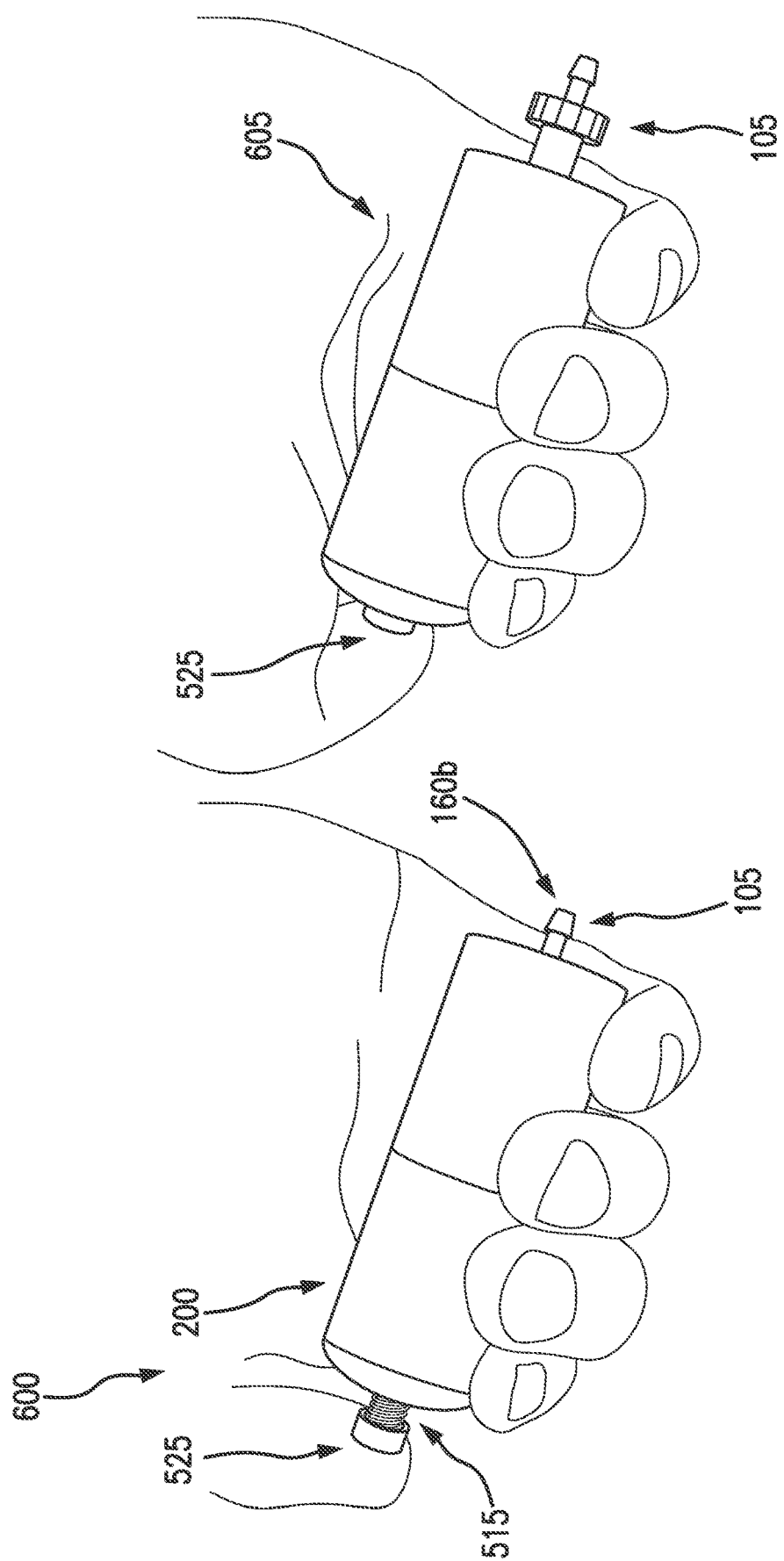
FIGS. 6A-6B illustrates exemplary embodiments of operation of a luer lock tool in accordance with the present disclosure.

In some embodiments, the luer lock tool 200 may be in a first position 600 as shown in FIG. 6A, where the spring 515 is in a neutral position. The luer lock fitting 105, and/or the individual male and/or female luer lock fitting 150, 160 may be disposed at least partially in the cavities 320, 325 of the respect tool base 205 and tool cap 210. For example, only the second end 160b of the female luer lock fitting 160 may be exposed at the open end 415 of the tool cap 210. When an operator pushes the ejection mechanism 250 into the luer lock tool 200 in a second position 605 as shown in FIG. 6B, the spring 515 may be compressed so that the rod 510 and the sleeve 520 extend further into the cavity 325 of the tool portion 310 of the tool base 205. When a male and/or female luer lock fitting are positioned in the tool base 205 and/or the tool cap 210, the ejection mechanism 250 may push the individual male and/or female luer lock fitting 150, 160, and/or the assembled luer lock fitting 105, out an open end 415 of the tool cap 210.

Figure 7:
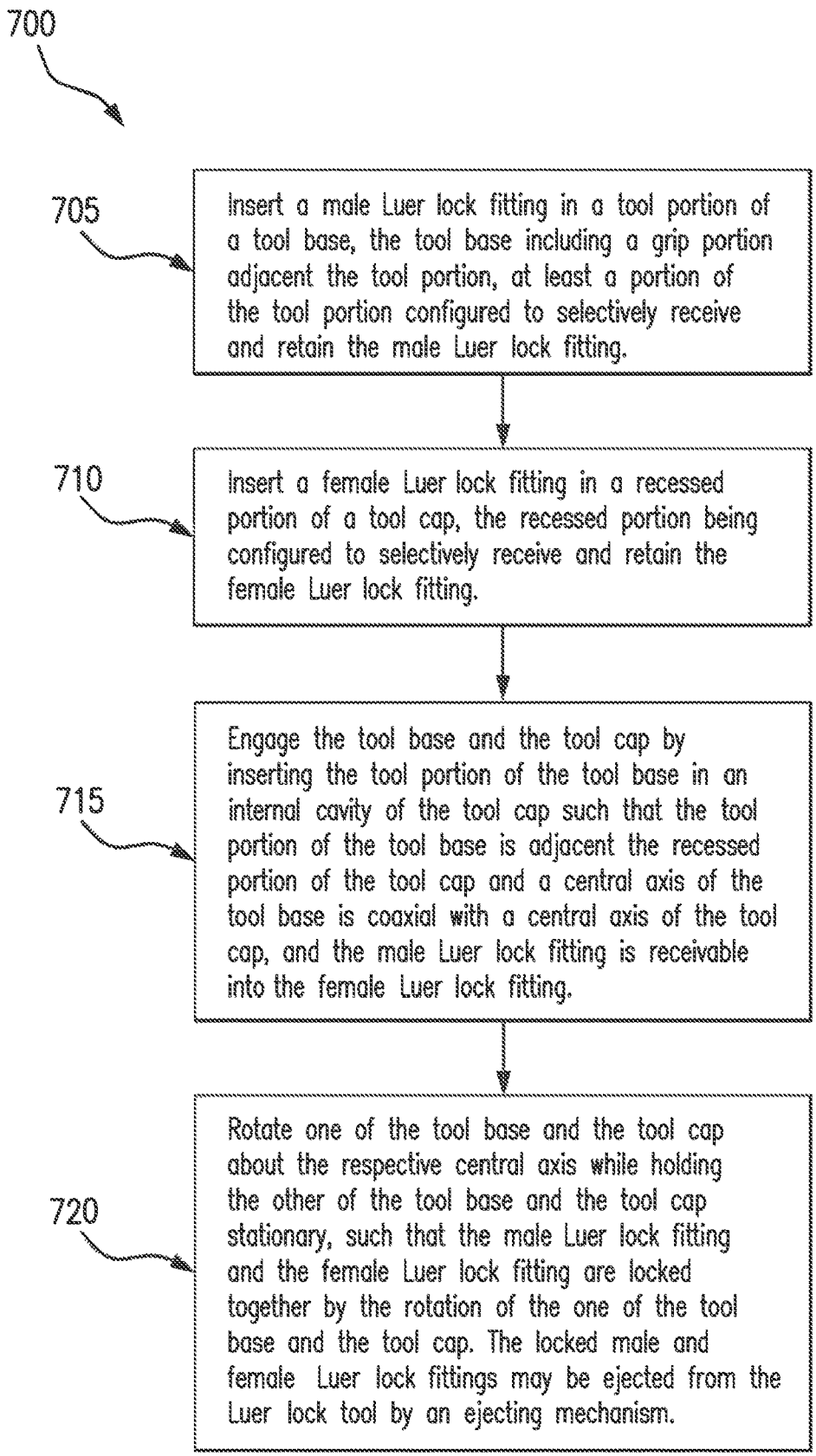
FIG. 7 is a flow diagram illustrating a method of assembling a male luer lock fitting and a female luer lock fitting in accordance with an embodiment of the present disclosure.

Referring now to FIG. 7, a flow diagram 700 illustrating a method of assembling a male luer lock fitting and a female luer lock fitting in accordance with an embodiment of the present disclosure is shown. At step 705, a male luer lock fitting is inserted in a tool portion of a tool base, the tool base including a grip portion adjacent the tool portion, at least a portion of the tool portion configured to selectively receive and retain the male luer lock fitting. At step 710, a female luer lock fitting is inserted in a recessed portion of a tool cap, the recessed portion being configured to selectively receive and retain the female luer lock fitting.

At step 715, the tool base and the tool cap are coupled together by inserting the tool portion of the tool base in an internal cavity of the tool cap such that the tool portion of the tool base is adjacent the recessed portion of the tool cap, and a central axis of the tool base is coaxial with a central axis of the tool cap. By coupling the tool cap and the tool base together in this manner, the male luer lock fitting is receivable into at least a portion of the female luer lock fitting. At step 720, one of the tool base and the tool cap may be rotated about its respective central axis, and the other of the tool base and the tool cap may remain stationary, so that the male luer lock fitting and the female luer lock fitting are locked together by the rotation of the one of the tool base and the tool cap. The locked male and female luer lock fittings may be ejected from the luer lock tool by an ejection mechanism. The ejection mechanism may include a rod and a spring, the rod and the spring being disposed at least partially in an internal cavity of the tool base and the internal cavity of the tool cap and coaxial to the tool base and the tool cap, wherein a first end of the rod and the spring is external to the tool base.

As used herein, an element or operation recited in the singular and proceeded with the word "a" or "an" should be understood as not excluding plural elements or operations, unless such exclusion is explicitly recited. Furthermore, references to "one embodiment" of the present disclosure are not intended to be interpreted as excluding the existence of additional embodiments that also incorporate the recited features.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are intended to fall within the scope of the present disclosure. Furthermore, although the present disclosure has been described herein in the context of a particular implementation in a particular environment for a particular purpose, those of ordinary skill in the art will recognize that its usefulness is not limited thereto and that the present disclosure may be beneficially implemented in any number of environments for any number of purposes. Accordingly, the claims set forth below should be construed in view of the full breadth and spirit of the present disclosure as described herein.

What is claimed is:

1. A luer lock tool, comprising:
    a tool base including a grip portion adjacent a tool portion, the grip portion having an outer diameter and an internal cavity, and the tool portion having an internal cavity and being configured to selectively receive and retain a male luer lock fitting at a first end of the cavity; and
    a tool cap having an outer diameter and an internal cavity, the tool cap including a recessed portion at an end configured to selectively receive and retain a female luer lock fitting;
    wherein the tool cap internal cavity is configured to receive at least a portion of the tool portion of the tool base;
    wherein at least one of the tool base and the tool cap are configured to rotate relative to the other of the tool base and the tool cap such that the male luer lock fitting and the female luer lock fitting are locked together by the rotation of the one of the tool base and the tool cap.

2. The luer lock tool according to claim 1, wherein the tool base and the tool cap are configured to engage together such that a central axis of the tool base and a central base of the tool cap are coaxial when the tool base and the tool cap are engaged.

3. The luer lock tool according to claim 1, wherein the recessed portion of the tool cap is configured to contact a flange of the female luer lock fitting, the recessed portion having a plurality of protrusions and recesses configured to engage with corresponding recesses and protrusions of the flange.

4. The luer lock tool according to claim 1, wherein the tool portion of the tool base is configured to contact the male luer lock fitting, the tool portion having a plurality of protrusions and recesses configured to engage with corresponding recesses and protrusions of the male luer lock fitting.

5. The luer lock tool according to claim 2, wherein one of the tool base and the tool cap are configured to remain stationary and the other of the tool base and the tool cap are configured to rotate about the respective central axis.

6. The luer lock tool according to claim 2, wherein the tool base and the tool cap are configured to rotate in opposite directions about the respective central axis.

7. The luer lock tool according to claim 1, wherein identification markings are disposed on at least one of the grip portion outer diameter of the tool base and the tool cap outer diameter.

8. The luer lock tool according to claim 1, wherein a plurality of notches are disposed on at least one of the grip portion outer diameter of the tool base and the tool cap outer diameter.

9. The luer lock tool according to claim 1, further comprising an ejection mechanism configured to selectively eject at least one of the male luer lock fitting and the female luer lock fitting.

10. The luer lock tool according claim 9, wherein the ejection mechanism includes a rod and a spring, disposed coaxially at least partially in the tool portion cavity and the grip portion cavity of the tool base.

11. The luer lock tool according to claim 10, wherein the spring is disposed adjacent a ledge in the grip portion cavity of the tool base and a cap is coupled to an end of the rod, the cap and the end of the rod being disposed external to the tool base.

12. The luer lock tool according to claim 10, wherein the ejection mechanism is configured to compress the spring such that the rod is configured to eject at least one of the male luer lock fitting and the female luer lock fitting out of the recessed portion end of the tool cap.

13. The luer lock tool according to claim 1, wherein when the tool base and the tool cap are engaged, the tool portion of the tool base is disposed adjacent the recessed portion of the tool cap.

14. The luer lock tool according to claim 1, wherein the tool base outer diameter and the tool cap outer diameter are equal.

15. A method for assembling a male luer lock fitting and a female luer lock fitting by a luer lock tool, the method comprising:
    inserting the male luer lock fitting in a tool portion of a tool base, the tool base including a grip portion adjacent a tool portion, at least a portion of the tool portion configured to selectively receive and retain the male luer lock fitting;

inserting the female luer lock fitting in a recessed portion of a tool cap, the recessed portion being configured to selectively receive and retain the female luer lock fitting;

engaging the tool base and the tool cap by inserting the tool portion of the tool base in an internal cavity of the tool cap such that the tool portion of the tool base is adjacent the recessed portion of the tool cap and a central axis of the tool base is coaxial with a central axis of the tool cap, and the male luer lock fitting is receivable into the female luer lock fitting; and rotating one of the tool base and the tool cap about the respective central axis while holding the other of the tool base and the tool cap stationary, such that the male luer lock fitting and the female luer lock fitting are locked together by the rotation of the one of the tool base and the tool cap.

16. The method according to claim 15, further comprising ejecting the locked male luer lock fitting and the female luer lock fitting by an ejection mechanism.

17. The method according to claim 16, wherein the ejection mechanism includes a rod and a spring, the rod and the spring disposed at least partially in an internal cavity of the tool base and an internal cavity of the tool cap and coaxial to the tool base and the tool cap, and a first end of the rod and the spring being external to the tool base.

18. The method according to claim 17, wherein the spring extends externally along the rod, and the spring is compressed between the first end of the rod and a ledge in an internal cavity of the tool base, a second end of the rod being disposed at least partially in the internal cavity of the tool cap such that the rod pushes the locked male and female luer lock fitting out of the recessed portion of the tool cap.

19. The method according to claim 15, wherein protrusions of the male luer lock fitting engage in recesses of the tool portion of the tool base, and recesses of the male luer lock fitting engage in protrusions of the tool portion of the tool base.

20. The method according to claim 19, wherein protrusions of a flange of the female luer lock fitting engage in recesses of the recessed portion of the tool cap, and recesses of the flange of the female luer lock fitting engage in protrusions of the recessed portion of the tool cap.

* * * * *